US012661089B2

(12) United States Patent
Sandrin et al.

(10) Patent No.: US 12,661,089 B2
(45) Date of Patent: Jun. 23, 2026

(54) ELASTOGRAPHY DEVICE AND METHOD

(71) Applicant: ECHOSENS SA, Paris (FR)

(72) Inventors: Laurent Sandrin, Bourg-la-Reine (FR);
Hugo Lorée, Nogent-sur-Marne (FR);
Véronique Miette, L'Hay-les-Roses
(FR)

(73) Assignee: ECHOSENS SA, Paris (FR)

( * ) Notice: Subject to any disclaimer, the term of this
patent is extended or adjusted under 35
U.S.C. 154(b) by 0 days.

(21) Appl. No.: 18/789,046

(22) Filed: Jul. 30, 2024

(65) Prior Publication Data

US 2026/0033807 A1      Feb. 5, 2026

(51) Int. Cl.
    *A61B 8/00*          (2006.01)
    *A61B 8/08*          (2006.01)
(52) U.S. Cl.
    CPC ............... *A61B 8/485* (2013.01); *A61B 8/08*
        (2013.01); *A61B 8/4209* (2013.01); *A61B*
        *8/4411* (2013.01); *A61B 8/4455* (2013.01);
                          *A61B 8/4494* (2013.01)
(58) Field of Classification Search
    CPC ......... A61B 8/485; A61B 8/08; A61B 8/4209;
            A61B 8/4411; A61B 8/4455; A61B
                                        8/4494
    See application file for complete search history.

(56) References Cited

U.S. PATENT DOCUMENTS

2008/0058644 A1* 3/2008 Sandrin ................ A61B 8/4209
                                                       600/459
2016/0106381 A1* 4/2016 Aase .................. A61B 17/3403
                                                       600/459
2016/0128670 A1* 5/2016 Morgan ............... A61B 8/4455
                                                       600/472
2019/0175144 A1* 6/2019 O'Brien ............... A61B 8/0816
2021/0295500 A1* 9/2021 Liu ....................... A61B 8/4461
2023/0011821 A1* 1/2023 Sandrin ................ A61B 8/4477
2023/0181158 A1* 6/2023 Tisa ..................... A61B 8/4483
                                                       600/459

FOREIGN PATENT DOCUMENTS

FR            2 875 695 A1      3/2006

OTHER PUBLICATIONS

Byenfeldt, M., et al., "Influence of Probe Pressure on Ultrasound-
Based Shear Wave Elastography of the Liver Using Comb-Push 2-D
Technology," Ultrasound in Medicine and Biology, vol. 45, Issue 2,
(Year: 2018), pp. 411-428.

* cited by examiner

*Primary Examiner* — Alexei Bykhovski
(74) *Attorney, Agent, or Firm* — CUSHMAN PARTNERS
LLC

(57)                ABSTRACT

A device for measuring the stiffness of an organ of a subject,
the measuring device including a measurement casing which
includes a) a shear wave emitter adapted to generate a
low-frequency elastic wave, and b) an ultrasound transducer
adapted to acquire ultrasound signals to determine the
stiffness of the organ based on the propagation of the
generated low-frequency elastic wave, and an applicator
extending from the measurement casing, the applicator
being adapted to be placed against a part of a body of the
subject, the applicator including a position maintenance
device for maintaining the transducer perpendicular to the
part of the body of the subject.

16 Claims, 8 Drawing Sheets

ELASTOGRAPHY DEVICE AND METHOD

FIELD

The present invention relates to the field of elastography, for example liver elastography. More specifically, the invention concerns a device for measuring the stiffness of an organ of a subject.

BACKGROUND

Measuring liver stiffness (LS) has been shown to be a very useful tool to help health care professionals detect or characterize liver disease or injuries, and more generally monitor the condition of the liver of a subject.

There are basically two kinds of elastography devices for liver stiffness measurement (LSM): imaging devices which derive the LSM from an image of stiffness using for example Shear Wave Elastography, SWE, (as detailed for example in "Influence of Probe Pressure on Ultrasound-Based Shear Wave Elastography of the Liver Using Comb-Push 2-D Technology", Byenfeldt, Marie et al. Ultrasound in Medicine and Biology, Volume 45, Issue 2, 411-428) and devices based on Vibration-Controlled Transient Elastography (hereinafter referred to as VCTE), such as the FibroScan® system.

With the FibroScan® system, an operator places the tip of a probe, that has a rather small diameter (typically comprised between 5 and 15 mm), in contact with the subject's body, in front of the expected area of a subject's liver. The operator then presses a button, triggering a transient, low frequency mechanical pulse delivered by the probe tip (the spectrum of this pulse is centered on a frequency comprised typically between 10 and 500 hertz). This pulse generates elastic waves that travel in the subject's body. Simultaneously, an ultrasound transducer mounted on the probe tip, in contact with the subject's body, emits a plurality of ultrasound shots into the tissue, with a high repetition rate, of 6 kilohertz for instance. The echo signals, corresponding to the backscattering of the different ultrasound shots emitted, are acquired by the probe to track slight movements of the tissue caused by the elastic waves passing through. The tracking is performed using correlation techniques applied to successive echo signals. The detected movements enable one to compound an elastic wave propagation image showing the tissue deformation both as a function of depth z, and as a function of time t, sometimes referred to as an "elastogram" (also called "strain map" or "displacements" or "shear wave propagation map").

In order to obtain a reliable measurement of liver stiffness, the tip of the probe must be placed precisely against the part of the subject's body (which is in front of the expected area of a subject's liver). Once the probe is correctly positioned, its position must be sustained at the same reliable measurement spot until the examination is completed. Incorrect positioning of the probe may lead to an overestimation of the liver stiffness (and thus subsequent misdiagnosis of the patient's condition).

However, as the tip of the probe presents a quite small dimension, it is difficult to ensure such an accurate positioning of the probe with respect to the body of the subject. Such positioning thus requires specific training for the operators, as some may place the transducer correctly while others may not. Furthermore, due to the delivered transient, low frequency mechanical pulses (and still the small diameter of the tip of the probe) and the use of an ultrasound coupling gel, the probe can slide over the surface of the body of the subject. This movement can distort liver stiffness measurements. Consequently, operators may struggle to maintain consistent contact between the probe and the subject's body. This task is further complicated because the operator's attention is focused on the screen rather than the probe during the examination. Furthermore, it has been seen that when the operator presses the button, the probe tends to tilt relative to the subject's body, leading to overestimations of liver stiffness.

SUMMARY

Various aspects of the present invention aim at improving the positioning of a probe used to measure the stiffness of an organ of a subject reliability, in order to obtain reliable measurements and to facilitate the implementation by the operator.

An aspect of the invention relates to a device for measuring the stiffness of an organ of a subject, the measuring device comprising:

a measurement casing which comprises:

a) a shear wave emitter adapted to generate a low-frequency elastic wave, and b) an ultrasound transducer adapted to acquire ultrasound signals to determine the stiffness of the organ based on the propagation of the generated low-frequency elastic wave, and an applicator extending from the measurement casing, the applicator being adapted to be placed against a part of a body of the subject, the applicator comprising a position maintenance device configured to maintain the transducer perpendicular to the part of the body of the subject.

In the present description, by "perpendicular", it is meant that an angle defined between a plane orthogonal to the transducer axis (and tangent to the transducer) and a plane tangent to the part of the body of the subject against which the transducer is applied is lower than 10 degrees.

Various aspects of the invention particularly relates to the measurement of the stiffness of the liver of a subject, but the invention can also apply to other organs of the body of the subject, such as the brain.

Beneficially, the applicator according to the invention allows a better positioning of the probe against the body of the subject thanks to the position maintenance device. An accurate position of the probe and a proper perpendicularity between the transducer and the body of the subject is thus ensured. Here, the perpendicularity is obtained in a simple way thanks this position maintenance device.

Aspects of the invention offer several benefits. Firstly, it increases the contact surface between the measuring device and the subject's body is larger, thus ensuring better transmission of the shear waves. This improvement enhances the accuracy of organ stiffness measurements by reducing variability caused by incorrect positioning of the probe.

Furthermore, the examination becomes more comfortable for the patient due to the larger contact surface, which distributes the applied pressure more evenly. The operator also benefits from this increased surface area, as it allows for easier handling of the measuring device and reduce slippage on the subject's skin during examination).

Beneficially, the ergonomics of the applicator are enhanced, further improving the overall user experience.

Other non-limiting and beneficial features of the invention, taken individually or according to all the combinations that are technically possible, are the following:

a tip supporting the transducer presents a shape of revolution about a transducer axis, the transducer being associated with a diameter d, the position maintenance device comprises a supporting surface adapted to be placed against the part of the body of the subject, the supporting surface being at a distance greater than two diameters d from the transducer axis;

a tip supports the transducer presenting a shape of revolution about a transducer axis, the position maintenance device comprises a supporting surface adapted to be placed against the part of the body of the subject, the supporting surface being at a distance comprised between 40 and 90 millimeters from the transducer axis;

a tip supports the transducer presents a shape of revolution about a transducer axis, the position maintenance device comprises a supporting surface adapted to be placed against the part of the body of the subject, a height being defined between the supporting surface and a free end of the transducer, the height being adjustable along the transducer axis;

the height is manually adjustable;

the height is automatically adjustable;

the applicator is mounted removable on the measurement casing;

the measurement device further comprises a mechanical system adapted to adjust automatically the height along the transducer axis;

the mechanical system comprises a screw device adapted to adjust automatically the height along the transducer axis;

the mechanical system comprises a retractable device adapted to adjust automatically the height along the transducer axis;

the applicator comprises a mounting system adapted to enable a rotation of the applicator around the transducer in order to adjust the position of the applicator with respect to the transducer;

the measurement casing comprises a locking mechanism adapted to lock the applicator in a measurement position relative to the measurement casing;

the applicator comprises at least two support portions extending from a surface of the measuring casing, the two support portions facing each other on either side of the transducer, the two support portions being adapted to be placed against the part of the body of the subject, each support portion comprising an end surface which presents a concave curvature with respect to a plane orthogonal to a transducer axis;

the applicator comprises a side surface extending from a surface of the measuring casing, the side surface defining a compartment which comprises the transducer, the side surface comprising an end surface with at least a first surface portion and a second surface portion, the first surface portion presenting a concave curvature with respect to a plane orthogonal to a transducer axis, the second surface portion presenting a convex curvature with respect to a plane orthogonal to the transducer axis:

the side surface of the applicator comprises two first surface portions facing each other on either side of the transducer and two second surface portions facing each other on either side of the transducer;

the end surface is continuous and surrounds the transducer;

the applicator comprises a material transparent to wavelengths in the visible range;

the applicator comprises a supporting surface adapted to be placed against the part of the body of the subject and a side surface extending between the measurement casing and the supporting surface, the side surface comprising at least one opening in order to see the transducer from outside of the measurement device;

the applicator comprises a polymer material;

the applicator comprises at least one indicator light configured to provide a positioning information of the applicator against the part of the body of the subject;

the measuring device further comprises an intercostal guide adapted to adjust the positioning of the transducer between two adjacent ribs of the subject;

the applicator comprises a detection system configured to detect and identify the use of the applicator during an examination of the subject;

the applicator comprises a supporting surface adapted to be placed against the part of the body of the subject, the supporting surface being provided with a membrane such that, when the applicator is placed against the part of the body of the subject, the membrane is placed between the transducer and the part of the body of the subject; and the membrane comprises an elastically deformable polymer material.

Other features and benefits of the invention disclosed herein will become apparent from the following description of non-limiting embodiments, with reference to the appended drawings.

BRIEF DESCRIPTION OF THE DRAWINGS

The present invention is illustrated by way of example, and not by way of limitation, in the figures of the accompanying drawings, in which like reference numerals refer to similar elements and in which.

DETAILED DESCRIPTION

Various aspects of the present invention aim at improving the measurements of the stiffness of an organ of a subject by ensuring an accurate positioning, with respect, or relative, to the body of the subject, of a device for measuring the stiffness. More particularly, an aspect of the invention relates to a measuring device that ensures the probe maintains an accurate position and a proper perpendicularity relative to the body of the subject.

An aspect of the invention thus relates to a measuring device 1 configured to measure the stiffness of an organ of a subject. An aspect of the invention particularly relates to the measurement of the stiffness of the liver of a subject, but the invention can also apply to other organs of the body of the subject, such as the brain.

FIGS. 1 to 3 and 14 represent a measuring device 1 according to an embodiment of the invention. The measuring device 1 comprises a measurement casing 3 and an applicator 10; 20.

The measurement casing 3 forms the main body of the measuring device 1. The measurement casing 3 is adapted to be handled by an operator, for example to perform the measurement of the stiffness of the organ of the subject. The shape and the design of the measurement casing 3 is not limited to the ones represented in FIGS. 1 to 3 and 14. It will be appreciated that any other shape and design may be used as long as they remain ergonomic and easy to hold and to use for an operator.

Figure 1:
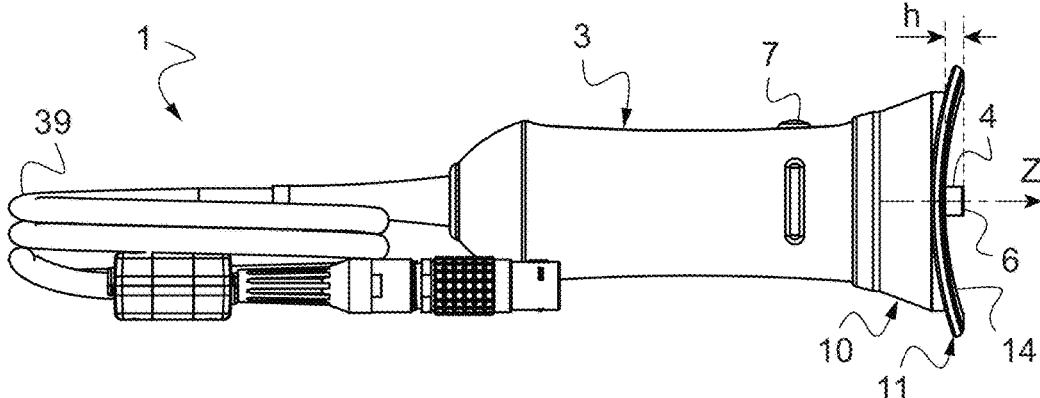
FIG. 1 represents a perspective view of a measuring device according to an embodiment of the invention.
Figure 2:
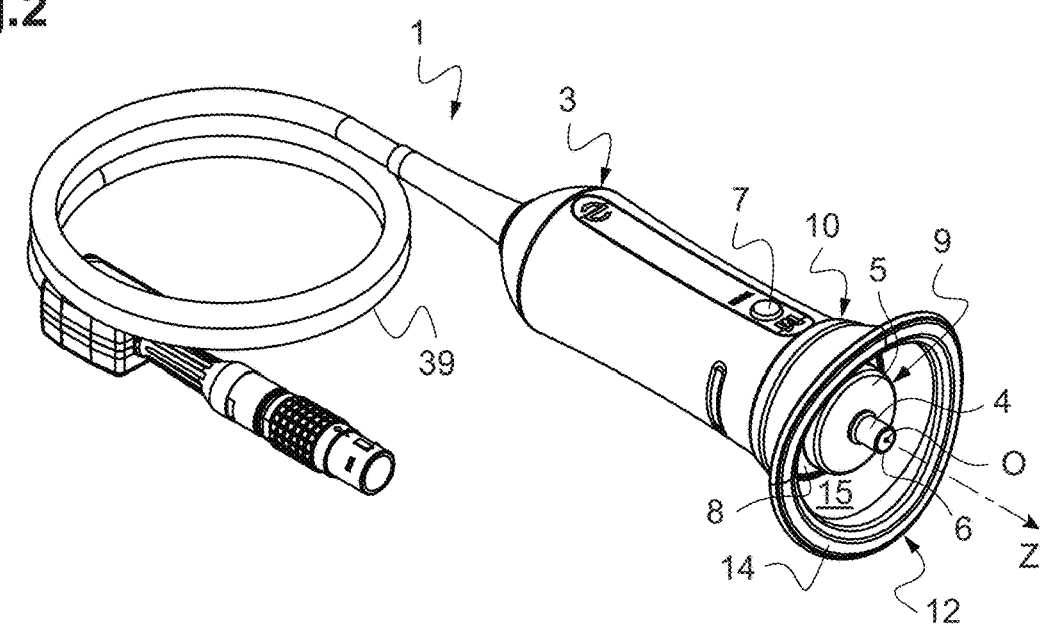
FIG. 2 represents another perspective view of the measuring device according to an embodiment of the invention.
Figure 3:
FIG. 3 represents another perspective view of the measuring device according to an embodiment of the invention.
Figure 3:
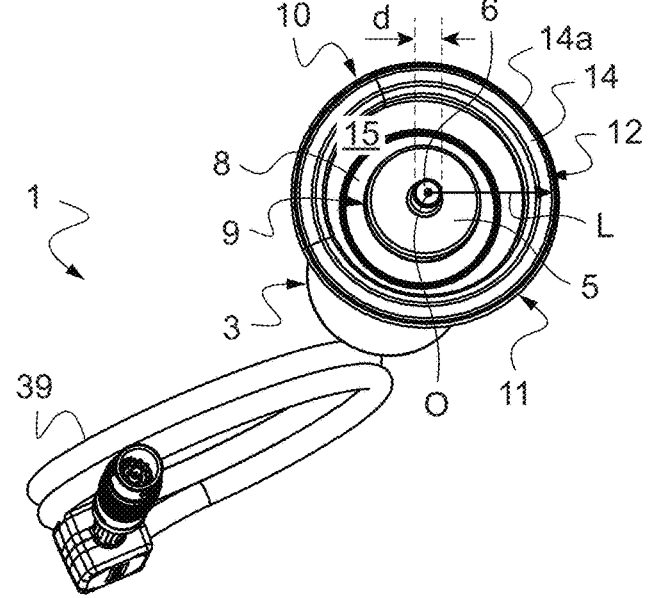

The measurement casing 3 is equipped with a probe 9. The probe 9 comprises a protruding part 5, which protrudes from the measurement casing 3, and a transducer 6. The probe 9 can thus be applied against the body of the subject, to deliver mechanical pulses to it, and to transmit and acquire ultrasound (U/S) shots. In this embodiment, the protruding part 5 comprises a tip 4, for instance a cylindrical tip (with here a circular transducer 6 at its end) as represented in FIGS. 1 to 3. As an alternative, the tip (and the corresponding transducer) can be of various shapes, such as rectangular, ellipsoidal or oblong.

In other embodiments, the protruding part could be an ultrasound head (located at an end of the probe) including an array, for instance a linear array of U/S transducers. In this regard, it will be appreciated that the proposed technique can be used with a single element ultrasound transducer (such as in FIGS. 1 to 3, which can be of various shapes: rectangular or ellipsoidal or circular for example), or with a multi-element ultrasound transducer (such as an array of U/S transducers, for example a linear or convex or phased array ultrasound probe). While a single element ultrasound transducer is adapted to display A-mode and M-mode ultrasound imaging, a multi element ultrasound transducer can also display a B-mode image allowing easier localization of the to-be-measured tissue. In the case of a multi element ultrasound transducer, at least one of the beamformed ultrasound lines is used to track how the mechanical pulses propagate. To this end, using the center beamformed ultrasound line (which is aligned with the probe axis) is beneficial, for symmetry considerations.

The measurement casing 3 also comprises a shear wave emitter (non-visible in FIGS. 1 to 3 and 14 because it is located inside the measurement casing 3) adapted to generate a low-frequency elastic wave. The term "low-frequency elastic wave" used herein intends to cover waves with a frequency between 20 Hz and 200 Hz. This shear wave emitter is associated with the transducer 6 (which is a U/S transducer), which is fixed at an end of the tip 4. The transducer 6 is adapted to measure the stiffness of the organ of the subject based on the propagation of the generated low-frequency elastic wave. The shear wave emitter is typically a vibrator, an electrodynamic transducer, a voice-coil or an ultrasound transducer associated with acoustic radiation force.

Here, the transducer 6, plays both the role of an ultrasound emitter and the role of an ultrasound receiver (alternatively). As an alternative, in other embodiments, the measurement casing may comprise an U/S emitter and an U/S receiver that are distinct from each other.

Here, as represented in FIGS. 1 and 2, a transducer axis Z can be associated with the transducer 6. In the embodiment of FIGS. 1 and 2, the tip 4 presents a shape of revolution about the transducer axis Z. The transducer axis Z thus passes through a center O of the transducer 6.

The transducer axis Z here corresponds to the axis of a low frequency vibrator comprised in the ultrasound emitter and used to actuate the tip 4. In the case of a cylindrical tip (FIGS. 1 to 3), the transducer axis Z corresponds to the axis of the cylindrical tip. In the case of a rectangular, ellipsoidal or oblong shape, the transduced axis corresponds to the longitudinal axis of revolution of the corresponding shape.

Furthermore, a diameter d is also used to define the transducer 6. For a cylindrical transducer 6 (as shown in FIGS. 1 to 3), the diameter d corresponds to the diameter of the circle which forms the base of the cylinder. In other embodiments where the transducer presents a different shape (such as rectangular, oblong, or ellipsoidal), the transducer's diameter is defined as the diameter of an equivalent circle with an area or surface equal to that of the actual shape. For example, if the transducer is rectangular, its diameter is considered to be the diameter of a circle with the same surface area as the rectangle. This approach allows for a standardized way of describing the transducer's size across various shapes.

The measurement casing 3 may be connected to a central unit (not represented) by a connection cable 19, or by a wireless link (e.g. via WiFi or BLUETOOTH® (a short-range wireless technology standard)).

The central unit may comprise an electronic unit (which comprises for example a processor and a memory) configured for instance (programmed via instruction stored in a memory) to control the measuring device 1 so that the measuring device 1 performs a series of measurements of the stiffness of the organ of the subject.

In one or more embodiments, the series of measurements of the stiffness of the organ of the subject may be performed in response to a manual triggering by the operator. This manual triggering may be achieved by actuating a push-button switch 7 arranged on the measurement casing 3, or by actuating a foot-switch, for instance. In such a case, when the operator determines based on one or more pieces of information, that the acquisition of the series of measurements can begin, the operator triggers acquisition of the measurements.

As an alternative, the series of measurements of the stiffness of the organ of the subject may be performed automatically, based on one or more pieces of information. For example, the measuring device 1 (more particularly the central unit) may be configured to determine whether one or more conditions are satisfied and to trigger the emission of the series of mechanical pulses when one or more or all necessary conditions are satisfied.

All necessary conditions may be met when the probe 9 is positioned in an accurate position with respect to the relevant part of the body of the subject. Beneficially, in an aspect of the present invention, in order to allow the positioning and the holding of the transducer 6 against the body of the subject, the measuring device 1 comprises here an applicator 10; 20. As shown in FIGS. 1 to 3, the applicator 10 is specifically configured, or constructed and arranged to surround the transducer 6 in order to ensure accurate positioning of the transducer 6. The applicator 10; 20 is adapted to be placed against the part of the body of the subject in order to perform the measurements of the stiffness of the organ of the subject.

As shown in FIGS. 5 to 7 and 9 to 13, the applicator 10; 20 comprises a side surface 18a, 19a; 28a, 29a provided with a rim 11 at one end. In the embodiments of FIGS. 5 to 7 and 9-13, the side surface 18a, 19a; 28a, 29a forms a conical shape. This rim 11 is adapted to be placed against the relevant part of the body of the subject. As shown in FIGS. 1 to 13, the rim 11 may be continuous or interrupted. As shown in FIGS. 1 to 3, the side surface 18a, 19a; 28a, 28b defines or forms a compartment 15 that houses the transducer 6.

In order to ensure the accurate positioning of the measuring device 1 against the body of the subject, the applicator 10; 20 comprises a position maintenance device, element, structure, assembly, component or mechanism 12 configured to, or constructed and arranged to, maintain the transducer 6 perpendicular to the relevant part of the body of the subject. The position maintenance device 12 acts as a position and/or orientation maintenance structure or stability enhancement structure that ensures proper orientation of the transducer relative to the relevant part of the subject's body.

In the present description, by "perpendicular", it is meant that an angle defined between a plane orthogonal to the transducer axis Z (and tangent to the transducer 6) and a plane tangent to the part of the body of the subject against which the transducer 6 is applied is lower than 10 degrees) (°.

In one or more embodiments, the position maintenance device 12 is located in or at the rim 11. The position maintenance device 12 comprises a supporting surface 14 which is adapted to be placed against the relevant part of the body of the subject. In other words, the supporting surface 14 forms a contact surface with the part of the body of the subject during an examination. The supporting surface 14 is thus shaped in order to allow for the maintaining of the transducer 6 perpendicular to the relevant part of the body of the subject.

Beneficially, in an embodiment of the present invention, the supporting surface 14 is positioned at distance L from the transducer axis Z which is greater than two diameters d. As visible in FIG. 3, the distance L is defined between the transducer axis Z (passing through the center O of the transducer 6) and an outer contour 14a of the supporting surface 14. This distance feature, corresponding to a large applicator, thus increases the outside perimeter of the contact surface between the probe and the relevant part of the body of the subject (this outside perimeter is thus significantly higher than the one of the transducer itself).

In an embodiment, the supporting surface 14 is positioned at a distance L from the transducer axis Z which is greater than three diameters d.

As an example, the distance L is comprised between 40 and 90 millimeters (mm). In an embodiment, the distance L is about 60 mm. The term "about" indicates that the distance may vary within a range of +/−10%.

Beneficially, in an embodiment of the present invention, in order to be able to adapt the applicator to the morphology of the subject, a height h, defined between the supporting surface 14 of the applicator 10; 20 and a free end of the transducer 6 along the transducer axis Z, is adjustable. In the present description, by "adjustable", it is meant that the height h defined between the supporting surface 14 of the applicator 10 and the free end of the transducer 6 can be changed. By "adjustable along the transducer axis Z", it is meant that the projection of the distance between the supporting surface 14 of the applicator 10 and the free end of the transducer 6 can be changed.

Here, this height h is tailored to the subject's morphology. For example, there might be 2 to 10 predetermined heights available, corresponding to different clothing size the subject may wear. Alternatively, or additionally, the height h may also be adjusted based on a specific contact force that is applied to the subject's body. As an example, the height may be set to achieve a contact force of about 6 Newtons (N). The term "about" indicates that the force may vary within a range of +/−10%.

Adjusting the height h is particularly beneficial as it allows one to optimize the transmission of the shear wave and the compression of the subcutaneous tissues. The height h may thus be greater for subjects with thick subcutaneous tissues compared to leaner subjects, who may require an applicator with a smaller height).

According to an embodiment, the height h is manually adjustable. By "manually", it is meant that the height h is adjusted by the operator. As an example, several applicators associated with different heights h may be used. In other words, each applicator corresponds to a predetermined height h (when mounted on the measurement casing 3). The operator thus chooses the applicator 10; 20 whose height is best adapted to the subject's morphology.

Figure 18:
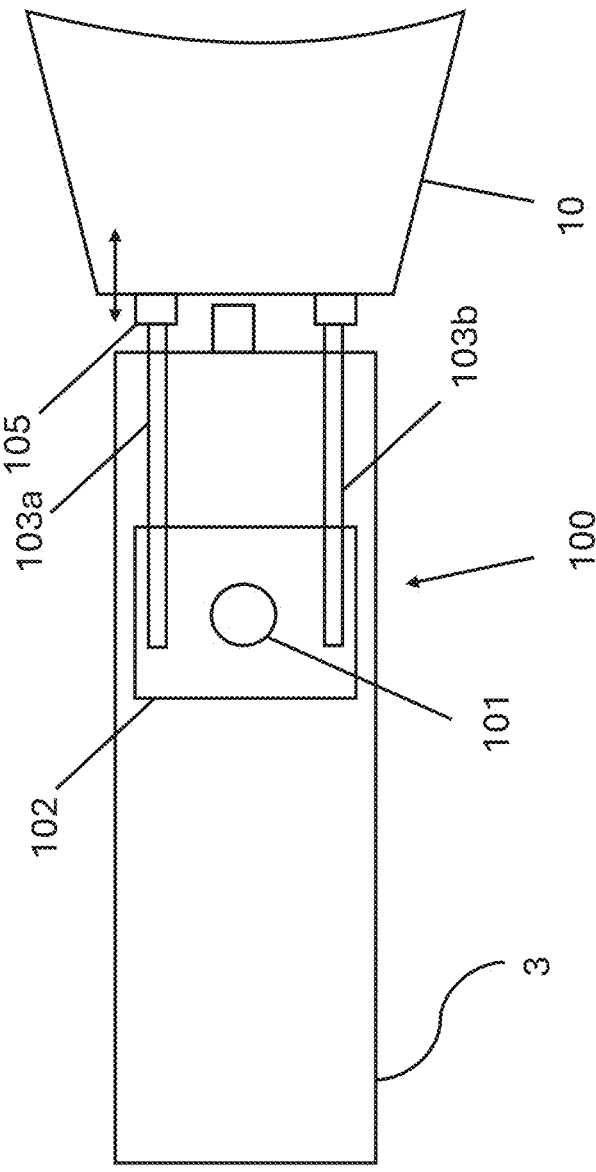
FIG. 18 schematically shows a measuring device according to an embodiment of the invention.

As another example, and referring to the embodiment of FIG. 18, the measurement casing 3 may comprise a height adjustment system 100 configured to manually adjust the height h. The height adjustment system 100 comprises a rotatable ring 101 coupled to a translation mechanism 102 configured to translate one or more arms 103a, b coupled to the applicator 10; 20 for adjusting the height h. This ring may be constructed similarly to the adjustment wheel found on beard trimmers for setting blade length. The ring may feature a plurality of fixed notches, each notch corresponding to a specific predetermined height. In FIG. 18, rotation of the ring 101 causes the arms 103*a, b* to translate via the translation mechanism 102 and change or adjust the height h. It will be appreciated that other mechanisms for translating the arms 103*a, b* could be used in other embodiments of the invention.

According to another embodiment, the height h is automatically adjustable. By "automatically", it is meant that the height h is adjusted without needing constantly the intervention of the operator, for example through the use of an electrical actuator. As an example, the measuring device 1 comprises a mechanical system (not represented in Figures) which is adapted to adjust automatically the height h along the transducer axis Z. For example, the mechanical system comprises a screw device adapted to adjust automatically the height h along the transducer axis Z. This screw device may allow a continuous adjustment of the height h. In a variant, the screw device may allow an adjustment by increments of 2 mm for example. For example, referring to FIG. 18, translation of the arms 103*a, b* could be achieved via a motor provided in the translation mechanism 102. The motor may be supplied with one or more inputs, such as for example one or more strain gauges that measure the pressure of the applicator 10;20 against the skin the patient, to provide the automatic adjustment of the height h.

As another example, the mechanical system may comprise a retractable device which is adapted to adjust automatically the height h along the transducer axis Z. The retractable device is for example adapted to slide the applicator along the transducer axis Z in order to change the height h along the transducer axis Z.

In an embodiment of the present invention, the different height h is about 0, 2, 4, 6 or 8 mm. The term "about" indicates that the height may vary within a range of +/−10%.

In order to ensure an accurate positioning of the measuring device 1 against the body of the subject, the applicator 10; 20 comprises at least two support portions 18; 28 which are adapted to be placed in contact with the part of the body of the subject to perform the measurements of the stiffness of the relevant organ. When the applicator 10; 20 is mounted on the measurement casing 3, these two support portions 18; 28 extend from a surface 8 of the measurement casing 3 from which the protruding part 5 protrudes.

Figure 5:
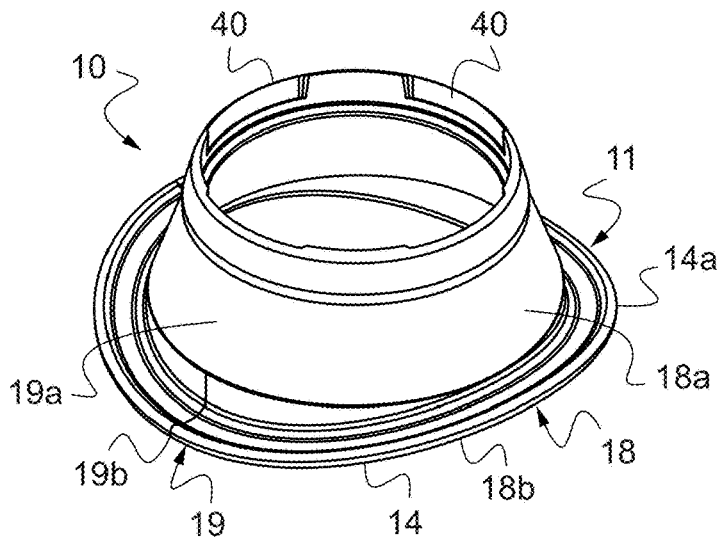
FIG. 5 represents a perspective view of the first example of the applicator comprised in the measuring device according to the invention.
Figure 7:
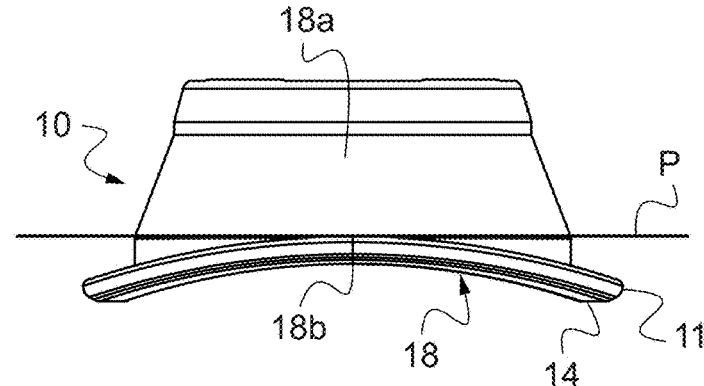
FIG. 7 represents another side view of the first example of the applicator comprised in the measuring device according to the invention.
Figure 8:
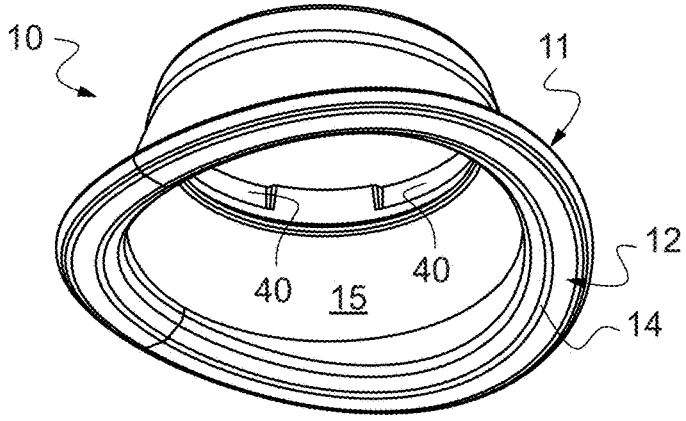
FIG. 8 represents another perspective view of the first example of the applicator comprised in the measuring device according to the invention.

As represented in FIGS. 5 and 7, each support portion 18; 28 comprises a portion of the side surface 18*a; 28a*. Each support portion 18; 28 also comprises an end surface 18*b; 28b*, which also forms the end of the side surface 18*a; 28a*. Each end surface 18*b; 28b* is adapted to be placed directly against the relevant part of the body of the subject. The end surfaces 18*b; 28b* are here part of the supporting surface 14 previously introduced.

As shown in FIGS. 2 and 3, the two support portions 18; 28 face each other on either side of the transducer 6 in order to optimize the perpendicular positioning of the measurement device 1 against the part of the body of the subject.

Beneficially, in an embodiment of the present invention, each end surface 18*b; 28b* presents a concave curvature with respect to a plane P orthogonal to the transducer axis Z. In other words, each end surface 18*b; 28b* presents a U-shape, the base of the U-shape is directed towards the side surface 18*a; 28a* whereas the ends of the branches of the U-shape are free. When the applicator 10; 20 is mounted on the measurement casing 3, the base of the U-shape is thus placed near or closer to the surface 8 of the measurement casing 3 whereas the ends of the branches of the U-shape are free, at the opposite of this surface 8. This concave curvature is particularly beneficial as it gives the applicator a shape that adapts to the body of the subject. With the described applicator 10, 20, the contact surface between the measuring device 1 and the body of the subject is larger, thus ensuring better transmission of the shear waves. It also improves the comfort of the subject during the examination as the pressure applied by the operator is distributed over a larger surface or area.

As a variant, the end surface of the applicator 10; 20 may be flat. As another variant, the end surface may present a convex curvature. It will be appreciated that a curvature radius of the end surface may be adapted to the morphology of the subject (in order to ensure that the supporting surface fits closely the part of the body of the subject).

In one or more embodiments of the invention, the applicator 10; 20 further comprises at least two other support portions 19; 29 which are adapted to be placed in contact with the part of the body of the subject to perform the measurements of the stiffness of the relevant organ. When the applicator 10; is mounted on the measurement casing 3, these two other support portions 19; 29 extend from the surface 8 of the measurement casing 3.

Figure 6:
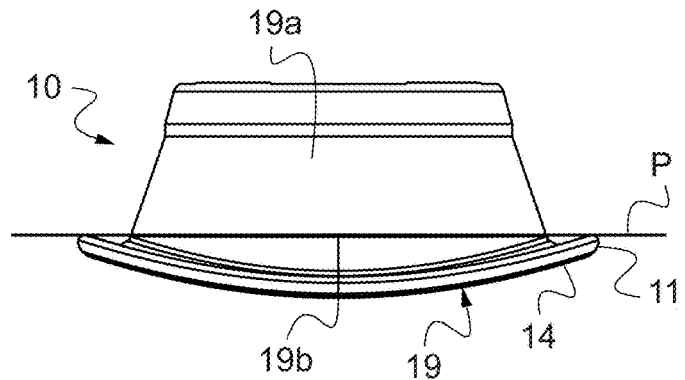
FIG. 6 represents a side view of the first example of the applicator comprised in the measuring device according to the invention.

As represented in FIGS. 5 and 6, each other support portion 19; 29 comprises a side surface 19*a; 29a* which extends from the surface 8 of the measurement casing 3. Each other support portion 19; 29 also comprises an end surface 19*b; 29b*, which also forms the end of the concerned side surface 19*a; 29a*. Each end surface 19*b; 29b* is adapted to be placed directly against the relevant part of the body of the subject. The end surfaces 19*b; 29b* are here parts of the supporting surface 14 previously introduced.

As shown in FIGS. 2 and 3, the two other support portions 19; 29 face each other on either side of the transducer 6 in order to optimize the perpendicular positioning of the measurement device 1 against the part of the body of the subject.

Beneficially, in an embodiment of the present invention, each end surface 19*b; 29b* presents a convex curvature with respect to a plane P orthogonal to the transducer axis Z. In other words, each end surface 19*b; 29b* presents an inverted U-shape, the ends of the branches of the inverted U-shape are directed towards the side surface 19*a; 29a* whereas the base of the inverted U-shape is free. When the applicator 10; 20 is mounted on the measurement casing 3, the ends of the branches of the inverted U-shape are placed near the surface 8 of the measurement casing 3 whereas the base of the inverted U-shape is free.

Therefore, as represented in FIGS. 5, 8, 10 and 11, the supporting surface 14 comprises alternating curvatures based on concave curvatures facing each other on either side of the transducer 6 and convex curvatures face each other on either side of the transducer 6. In the described embodiments, a convex curvature is positioned between two concave curvatures. In one or more, the applicator may include more than two concave curvatures and more than two convex curvatures.

The combination of the two support portions with an end surface with a concave curvature and two other support portions with an end surface with a convex curvature provides a close fit to the shape of the body of the subject. The contact surface between the measuring device 1 and the body of the subject is larger, thus ensuring better transmission of the shear waves. It also improves the comfort of the subject during the examination as the pressure applied by the operator is distributed over a larger surface.

According to a first example of the applicator 10 represented in FIGS. 1 to 8, the supporting surface 14 is continuous and surrounds the transducer 6. This design improves the applicator's ergonomics and enhances patient comfort by distributing the applied pressure over a larger surface or area. Additionally, the larger contact surface makes the examination easier for the operator by reducing the device's tendency to slide on the subject's skin (especially when a gel is provided on the patient's skin before applying the probe against the subject's skin).

The second example of the applicator 20 represented in FIGS. 9 to 13, incorporates a discontinuous or interrupted supporting surface 24. As shown in FIGS. 9 to 12, the side surface 29a comprises here two openings 30. Each opening 30 is formed at the junction of the side surface 29a and the convex-curved end surface 29b. The support portions with the concave curvature remain unmodified, maintaining accurate device positioning. These openings in the applicator's side surface provide a significant benefit: they allow the operator to visually confirm the correct positioning of the tip 4 and transducer 6 against the relevant part of the subject's body during the examination, without needing to move the measuring device 1.

Figure 4:
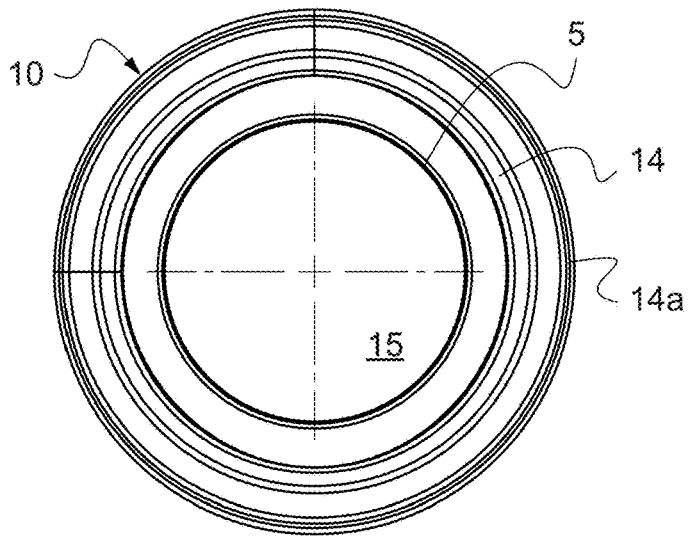
FIG. 4 represents a view of a first example of an applicator comprised in the measuring device according to the invention in a plane orthogonal to a transducer axis.
Figure 9:
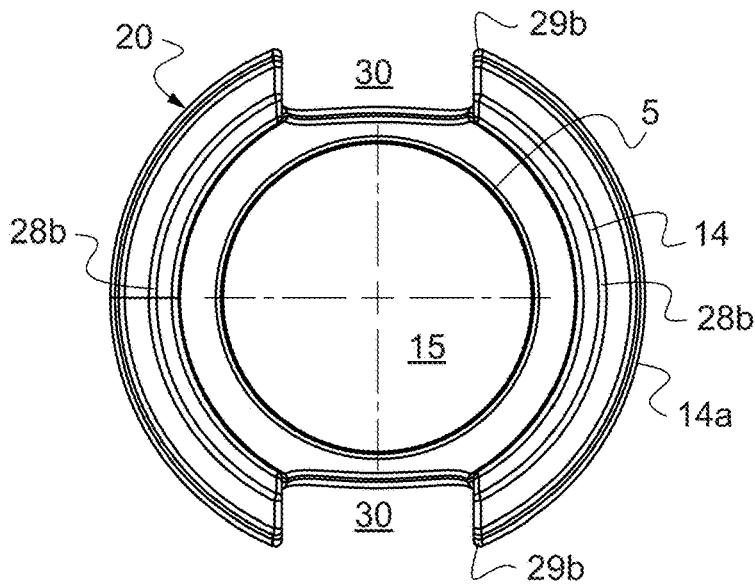
FIG. 9 represents a view of a second example of an applicator comprised in the measuring device according to the invention in a place orthogonal to a transducer axis.
Figure 10:
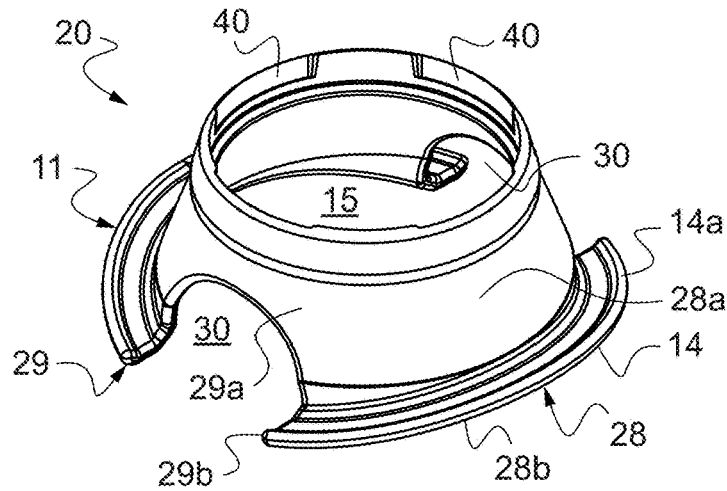
FIG. 10 represents a perspective view of the second example of the applicator comprised in the measuring device according to the invention.
Figure 11:
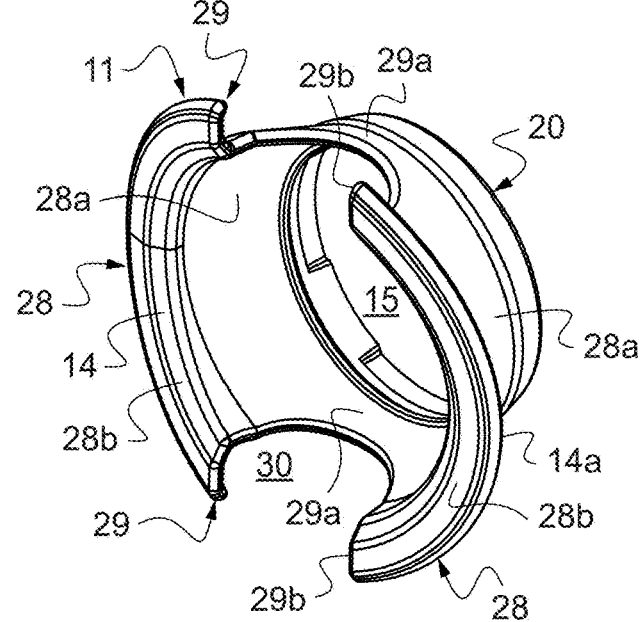
FIG. 11 represents another perspective view of the second example of the applicator comprised in the measuring device according to the invention.
Figure 12:
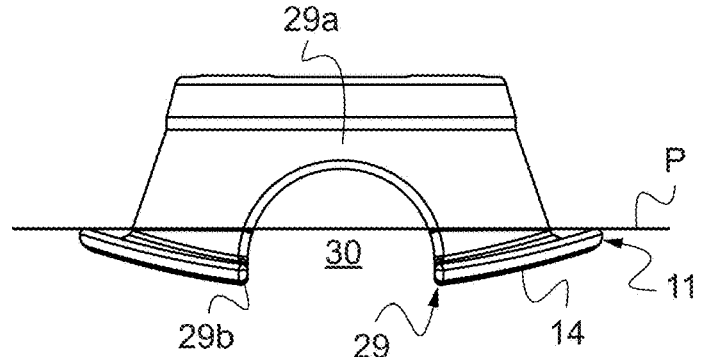
FIG. 12 represents a side view of the second example of the applicator comprised in the measuring device according to the invention.
Figure 13:
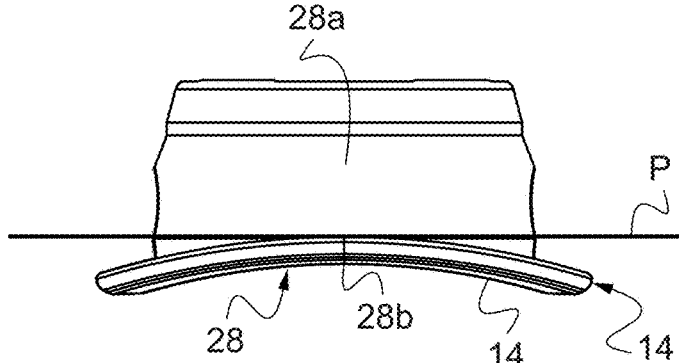
FIG. 13 represents another side view of the second example of the applicator comprised in the measuring device according to the invention.

Regardless of the example of the applicator 10; 20, as represented in FIGS. 4 and 9, the contact surface S between the applicator 10; 20 (more particularly, the supporting surface 14) and the part of the body of the subject is here roundly shape. In an embodiment, this contact surface S is here a disk.

In one or more embodiments, the applicator 10; 20 comprises a material transparent to wavelengths in the visible range. This transparency allows for the operator to see the tip 4 and the transducer 6 from outside of the measuring device 1, in order to check the correct positioning of the transducer against the relevant part of the body of the subject during the examination.

As an alternative, the side surface 18a, 19a; 28a, 29a comprises another opening (not represented) in order to see the transducer 6 from outside of the measuring device 1. This other opening allows the operator to see the tip 4 and the transducer 6, in order to check the correct positioning of the transducer during the examination.

The applicator 10; 20 here comprises a polymer material. In an embodiment, the applicator 10; 20 comprises a deformable polymer material. In the present description, a deformable polymer material is defined as a polymer material with a Shore 00 hardness lower than 50, such as, for example, comprised between 10 and 50. As an example, the applicator 10; 20 comprises a styrene-ethylene butadiene-styrene (SEBS) copolymer.

Deformable polymer materials are particularly beneficial for the applicator, as they allow it to conform to the subject's body curvature, thereby enhancing contact between the measuring device and the subject's body and improving examination quality.

More particularly, using a deformable polymer material enables the supporting surface to be bendable, flex and closely fit the relevant body part. This maximizes contact between the measuring device 1 and the subject's body part, helping to prevent tilting of the measuring device 1 during the examination. This improved larger contact is particularly beneficial for maintaining accurate probe positioning, even when the operator presses the push-button switch.

In one or more embodiments, the applicator may comprise at least one sensor adapted to assess or evaluate the positioning against the subject's body part or to measure the force applied by the operator. The sensor readings may be transmitted to the central unit to provide feedback and inform the operator. The sensor readings may be processed and/or fed to a motor (such as in the embodiment of FIG. 18) to automatically adjust the position of the applicator 10;20 relative to the transducer 6 and the height h. For example, referring to FIG. 19, the applicator 10; 20 comprises one or more sensors 110 (e.g. strain gauges) configured to determine a force applied by the applicator 10; against the skin of the patient.

In one or more embodiments, the applicator 10; 20 and/or the casing 3 may comprise at least one light indicator configured to provide a positioning information of the applicator against the part of the body of the subject. The light indicator may also provide an information related to the applied force. The light indicator may include a Light-emitting Diode (LED). For example, referring to FIG. 20, the casing 3 includes a plurality of LEDs 120 to provide the positioning information and/or force measurement. The casing 3 of FIG. may also include the sensors 110 shown in FIG. 19.

In an embodiment, the light indicator may be located at the base of the applicator 10; 20 (more particularly at the free end which is opposite to the contact surface S). For example, the light indicator presents an annular shape that follows, for example, the shape of the base of the applicator. In an embodiment, the light indicator (e.g. the LED) is molded at the free end of the applicator 10; 20. The material of the applicator 10; 20 may be transparent to visually see light emitted by the light indicator or LED. The light indicator may be powered by one or more cables provided on or in the applicator 10; and adapted to be connected via a connector to the measurement device 1. In an embodiment, the one or more cables may be molded within the applicator 10; 20. The connector for connecting the one or more cables to the measurement device 1 may be provided at the locking system 40.

As an example, the light indicator may be controlled by the central unit based on the measurement acquired by the sensor. For example, the light indicator may be green when the positioning of the applicator is correct and red when the positioning information corresponds to an incorrect positioning of the applicator against the part of the body of the subject.

In one or more embodiments, the applicator may comprise a detection system that allows for identification and detection (for example by the central unit) of the applicator, and particularly the height h, during the examination. Such detection system ensures proper use of the applicator and the measuring device. It also enables post-examination quality control by providing information such as whether an applicator was used and which type was employed.

In an embodiment, the detection system is for example based on Radio Frequency Identification (RFID) or on Near-Field Communication (NFC). The detection system may include a coil antenna positioned at the base of the applicator (more particularly at the free end which is opposite to the contact surface S). In a variant, the coil antenna may be placed in the side surface 18a, 19a; 28a, 29b of the applicator 10; 20.

In one or more embodiments (not represented), the applicator may comprise an identification system that allows the operator to identify which applicator is used. In other words, the identification system serves as a marking system for the applicator, allowing easy recognition of which applicator is in use, particularly its specific height h.

In an embodiment, the identification system is for example a color marking placed on the applicator (the color corresponding to a predefined height). As an example, the identification system is a colored ring positioned at the base of the applicator, which color ring follows for example the shape of the base of the applicator.

In one or more embodiments (not represented), the measuring device may comprise an intercoastal guide adapted to adjust the positioning of the transducer between two adjacent ribs of the subject. This intercoastal guide thus helps the operator to position the measuring device against the part of the body of the subject in order to perform a reliable examination.

Figure 14:
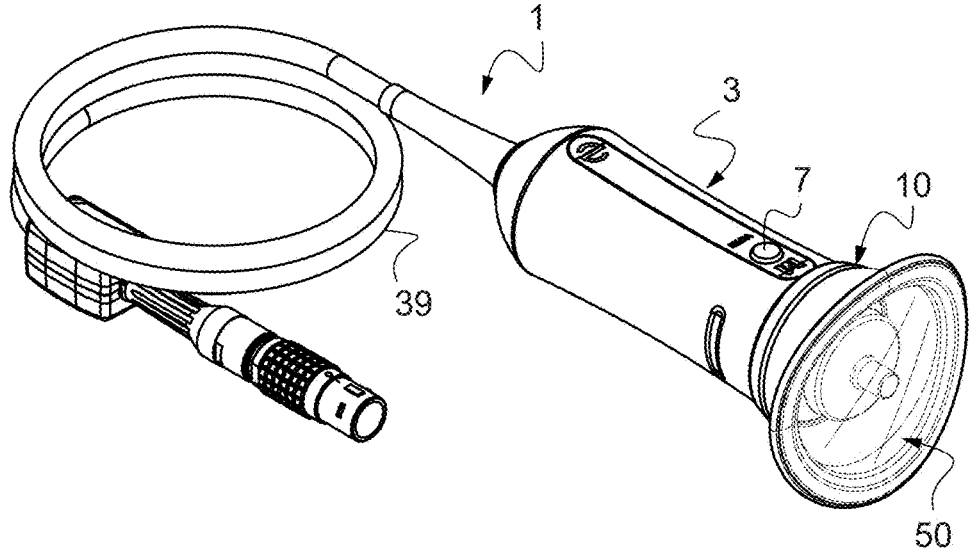
FIG. 14 represents a perspective view of another example of the measuring device according to the invention.
Figure 15:
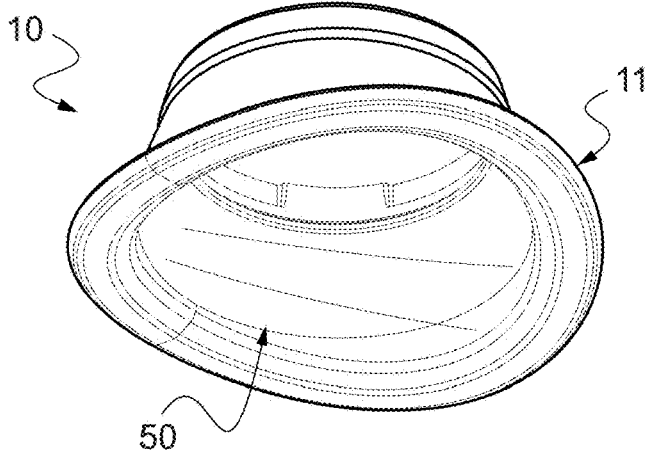
FIG. 15 represents a perspective view of an example of the applicator comprised in the measuring device of FIG. 14.

In one or more embodiments represented in FIGS. 14 and 15, the measuring device 1 comprises a membrane 50 fixed to the supporting surface 14 of the applicator 10. When the applicator 10 is placed against the part of the body of the subject, the membrane 50 is positioned between the transducer 6 and the considered part of the body of the subject. The membrane 50 offers several benefits. It enhances the subject's comfort during the examination, while also improving sanitary conditions. By preventing direct contact between the transducer 6 and the subject's body, the membrane facilitates better sterilization. This is particularly beneficial because the transducer, which is challenging to clean thoroughly, remains uncontaminated across multiple patient examinations.

Here, the membrane 50 comprises an elastically deformable polymer material. By "elastically deformable", it is meant that the material is able to take the shape of the part of the body of the subject and returns to its original shape after use. The same membrane can thus be used for multiple subjects or different body parts of the same subject without retaining any effects from previous examinations.

The membrane 50 comprises a polymer material. It comprises for example polyurethane, nitrile, vinyl or latex.

The applicator 10; 20 is mounted on the measurement casing 3, more particularly from the surface 8 of the measurement casing 3 from which the protruding part 5 protrudes from the measurement casing 3. In practice, the applicator 10; 20 is removably mounted on the measurement casing 3. In the present description, by "removably" or "removable", it is meant that the applicator can be easily placed on and removed from the measurement casing 3. The applicator's removability is particularly beneficial, as it allows for easy cleaning of the applicator after use. It also enables interchanging applicators based on the subject's characteristics, especially their body morphology.

Figures 19, 20:
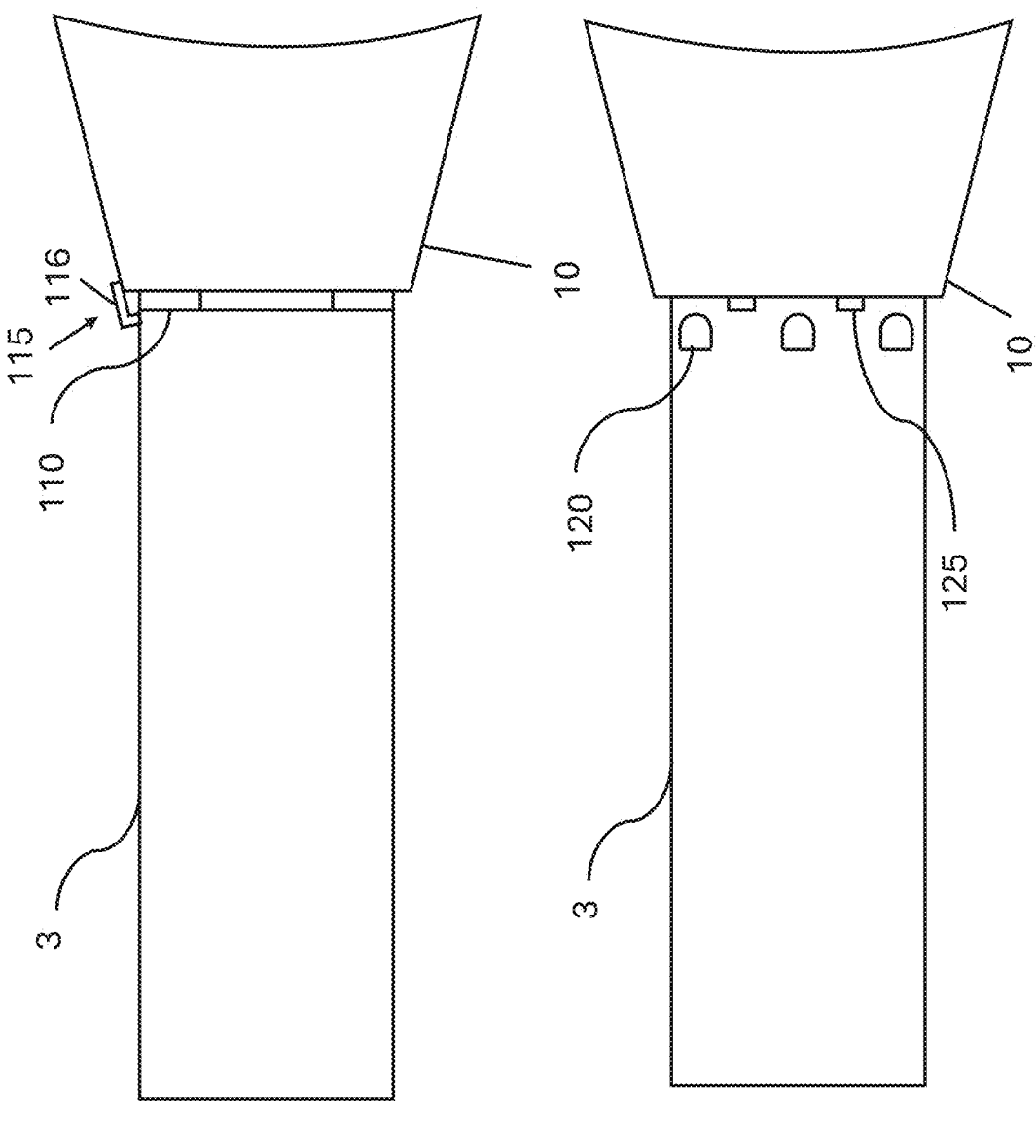
FIG. 19 schematically shows a measuring device according to an embodiment of the invention, and FIG. 20 schematically shows a measuring device according to an embodiment of the invention.

In an embodiment, the applicator 10; 20 is mounted on the measurement casing 3 by one or more clips, screws or springs 125 (which are schematically shown in FIG. 20).

Beneficially, the use of springs provides several benefits. It allows for movement of the supporting surface and enables adjustment of the force applied by the operator. Additionally, it contributes to the adjustment of the height between the applicator's supporting surface 14 and the free end of the transducer 6 along the transducer axis Z.

In one or more embodiments, the measurement casing 3 comprises a mounting system adapted to enable a rotation of the applicator 10; 20 around the transducer 6 (more particularly around the transducer axis Z). This mounting system allows adjustment of the position of the applicator 10; 20 with respect to the transducer 6. As an example, the position of the applicator 10; 20 may be adjusted in rotation in order to make it easier for the operator to hold the measuring device 1, for example by making the push-button switch 7 easily accessible. An example of the mounting system is schematically shown in FIG. 18, which shows a mounting system 105 provided at the end of the arms 103a, b that enables rotation of the applicator 10, 20 relative to the arms 103 a, b. The mounting system 105 may include arc shaped slots through which the arms 103a, b extend. Rotation of the applicator 10; 20 changes the positions of the arms 103a, b along the arc shaped slots. This is not limiting. Other types of mechanisms for rotating the applicator 10; 20 relative to the casing 3 may be used in other embodiments. For example, in an embodiment, the applicator 10; 20 may be clipped to the end of the casing 3 via a clip that allows for rotation of the applicator 10; 20 relative to the casing 3.

In one or more embodiments, the measurement casing 3 comprises a locking mechanism adapted to lock the applicator 10; 20 in a measurement position relative to the measurement casing 3. The applicator 10; 20 comprises complementary locking system 40 adapted to cooperate with the locking mechanism of the measuring device 1. In other words, the locking mechanism allows for the blocking of the applicator 10; 20 in a position in which the examination can be performed, by cooperating with the complementary locking system 40. In connection with the embodiment of FIG. 5, the locking mechanism may be formed at the end of the casing 3 (e.g. at the external surface of the casing 3) and may have a shape that is complementary to the shape of the complementary locking system 40. The locking mechanism and the complementary locking system 40 are configured to engage each other to lock the applicator 10; 20 in position. The measurement position corresponds for example to the one in which the operator can easily access the push-button switch 7 and perform the examination comfortably (without efforts).

In an embodiment, the locking mechanism and the complementary locking system 40 is a snap-in system. Alternatively or additionally, and as shown in FIG. 19, a locking mechanism 115 may include a removable fastener to removably fasten and/or lock the applicator 10; 20 in position relative to the casing 3. The fastener may include an arm 116 (e.g. an elastic arm) extending from the surface of the casing to be fastened to the applicator 10; 20. The arm 116 may engage one or more notches formed on the applicator 10;20 external surface to lock the applicator 10; 20 in position relative to the casing 3.

Figure 16:
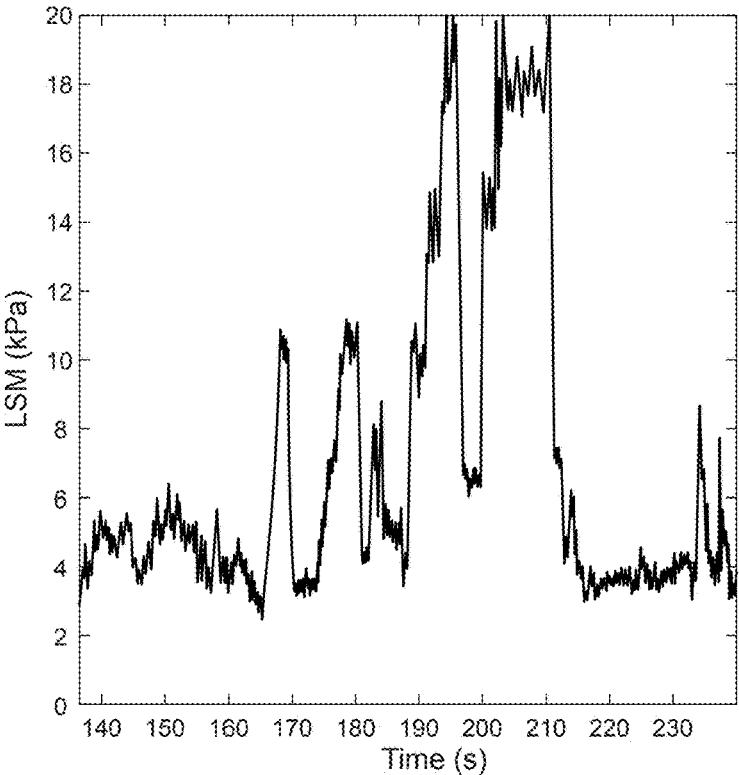
FIG. 16 represents the variability of the stiffness of an organ as a function of time with a measuring device according to the state of the art.
Figure 17:
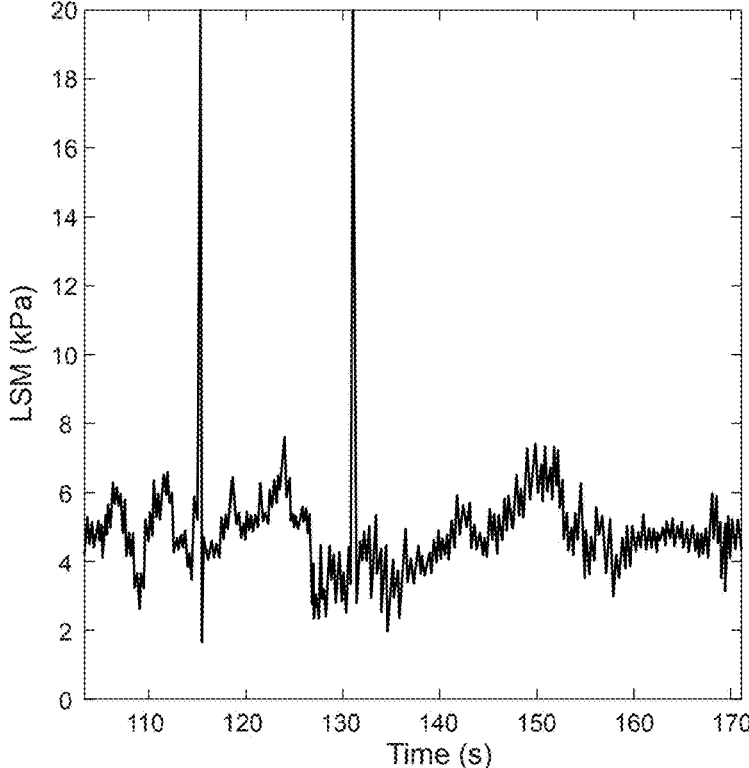
FIG. 17 represents the variability of stiffness of an organ as a function of time with a measuring device according to invention.

FIG. 16 represents the variability of the stiffness of an organ as a function of time without the applicator (with a measuring device according to the state of the art). FIG. 17 represents the variability of stiffness of an organ as a function of time with the applicator (with the measuring device according to the present invention).

As visible in FIG. 16 and FIG. 17, the use of the applicator in the measuring device allows one to obtain a more stable stiffness. The variability of the stiffness is more important without using the applicator.

Beneficially, the applicator according to an embodiment of the invention allows for a better positioning of the probe against the body of the subject thanks to the position maintenance device. An accurate position of the probe and a proper perpendicularity between the transducer and the body of the subject is thus ensured. Here, the perpendicularity is obtained in a simple way thanks to the position maintenance device.

One or more embodiments of the invention provide a larger contact surface between the measuring device 1 and the subject's body, ensuring better transmission of shear waves. This improves organ stiffness measurement by reducing variability caused by incorrect probe positioning.

Moreover, the larger contact surface enhances patient comfort during the examination by distributing the operator-applied pressure over a wider area. It also simplifies the examination process for the operator, as the increased contact surface reduces the likelihood of the measuring device sliding on the subject's skin.

Beneficially, ergonomics of the applicator are also improved.

The articles "a" and "an" may be employed in connection with various elements, components, processes or structures described herein. This is merely for convenience and to give a general sense of the elements, components, processes or structures. Such a description includes "one or at least one" of the elements or components. Moreover, as used herein, the singular articles also include a description of a plurality of elements or components, unless it is apparent from a specific context that the plural is excluded.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

Expressions such as "comprise", "include", "incorporate", "contain", "is" and "have" are to be construed in a non-exclusive manner when interpreting the description and its associated claims, namely construed to allow for other items or components which are not explicitly defined also to be present. Reference to the singular is also to be construed in be a reference to the plural and vice versa.

A person skilled in the art will readily appreciate that various parameters disclosed in the description may be modified and that various embodiments disclosed may be combined without departing from the scope of the invention. For example, various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Having described above several aspects of at least one embodiment, it is to be appreciated various alterations, modifications, and improvements will readily occur to those skilled in the art. Such alterations, modifications, and improvements are intended to be aspects of this disclosure. Accordingly, the foregoing description and drawings are by way of example only.

The invention claimed is:

1. A device for measuring a stiffness of an organ of a subject, the measuring device comprising:
a measurement casing which comprises:
a) a shear wave emitter adapted to generate a low-frequency elastic wave, and b) an ultrasound transducer adapted to acquire ultrasound signals to determine the stiffness of the organ based on a propagation of the generated low-frequency elastic wave, and
an applicator extending from the measurement casing, the applicator being adapted to be placed against a part of a body of the subject and configured to maintain the ultrasound transducer perpendicular to the part of the body of the subject, the applicator comprising (a) a side surface comprising one or more wall portions extending away from the measurement casing about an ultrasound transducer axis and defining a compartment that comprises the ultrasound transducer, the one or more wall portions being inclined with respect to the ultrasound transducer axis such that a lateral extent of the compartment increases from the measurement casing toward the part of the body of the subject and (b) a supporting surface connected to the side surface and adapted to be placed against the part of the body of the subject during measurement of the stiffness.

2. The measuring device according to claim 1, wherein the ultrasound transducer is supported by a tip, the tip presenting a shape of revolution about the ultrasound transducer axis, the ultrasound transducer being associated with a diameter d, said supporting surface adapted to be placed against the part of the body of the subject, the supporting surface being at a distance L greater than two diameters d from the ultrasound transducer axis.

3. The measuring device according to claim 1, wherein the ultrasound transducer is supported by a tip, the tip presenting a shape of revolution about the ultrasound transducer axis, said supporting surface adapted to be placed against the part of the body of the subject, the supporting surface being at a distance L comprised between 40 and 90 millimeters from the ultrasound transducer axis.

4. The measuring device according to claim 1, wherein the ultrasound transducer is supported by a tip, the tip presenting a shape of revolution about the ultrasound transducer axis, said supporting surface adapted to be placed against the part of the body of the subject, a height h being defined between the supporting surface and a free end of the ultrasound transducer, said height h being adjustable along the ultrasound transducer axis.

5. The measuring device according to claim 4, wherein the height h is manually adjustable.

6. The measuring device according to claim 4, wherein the height h is automatically adjustable.

7. The measuring device according to claim 1, wherein the applicator is mounted removable on the measurement casing.

8. A device for measuring a stiffness of an organ of a subject, the measuring device comprising:
a measurement casing which comprises:
a) a shear wave emitter adapted to generate a low-frequency elastic wave, and
b) an ultrasound transducer adapted to acquire ultrasound signals to determine the stiffness of the organ based on a propagation of the generated low-frequency elastic wave, and
an applicator extending from the measurement casing, the applicator being adapted to be placed against a part of a body of the subject and configured to maintain the ultrasound transducer perpendicular to the part of the body of the subject,
wherein the applicator comprises a mounting system adapted to enable a rotation of the applicator around the ultrasound transducer in order to adjust the position of the applicator with respect to the ultrasound transducer.

9. The measuring device according to claim 1, wherein the measurement casing comprises a locking mechanism adapted to lock the applicator in a measurement position relative to the measurement casing.

10. The measuring device according to claim 1, wherein the applicator comprises at least two support portions extending from a surface of the measurement casing, the two support portions facing each other on either side of the ultrasound transducer, the two support portions being adapted to be placed against the part of the body of the subject, each support portion comprising an end surface which presents a concave curvature with respect to a plane orthogonal to the ultrasound transducer axis.

11. A device for measuring a stiffness of an organ of a subject, the measuring device comprising:

a measurement casing which comprises:

a) a shear wave emitter adapted to generate a low-frequency elastic wave, and b) an ultrasound transducer adapted to acquire ultrasound signals to determine the stiffness of the organ based on a propagation of the generated low-frequency elastic wave, and an applicator extending from the measurement casing, the applicator being adapted to be placed against a part of a body of the subject and configured to maintain the ultrasound transducer perpendicular to the part of the body of the subject, wherein the applicator comprises a side surface extending from a surface of the measurement casing, the side surface defining a compartment which comprises the ultrasound transducer, the side surface comprising an end surface with at least a first surface portion and a second surface portion, the first surface portion presenting a concave curvature with respect to a plane orthogonal to an ultrasound transducer axis, the second surface portion presenting a convex curvature with respect to a plane orthogonal to the ultrasound transducer axis.

12. The measuring device according to claim 11, wherein the side surface of the applicator comprises two first surface portions facing each other on either side of the ultrasound transducer and two second surface portions facing each other on either side of the ultrasound transducer.

13. The measuring device according to claim 11, wherein the end surface is continuous and surrounds the ultrasound transducer.

14. The measuring device according to claim 1, wherein the applicator comprises a material transparent to wavelengths in the visible range.

15. The measuring device according to claim 1, wherein the applicator comprises a supporting surface adapted to be placed against the part of the body of the subject, the supporting surface being provided with a membrane such that, when the applicator is placed against the part of the body of the subject, the membrane is placed between the ultrasound transducer and the part of the body of the subject.

16. The measuring device according to claim 15, wherein the membrane comprises an elastically deformable polymer material.

\* \* \* \* \*